United States Patent [19]

Bergel et al.

[11] Patent Number: 4,971,668

[45] Date of Patent: Nov. 20, 1990

[54] PROCESS FOR THE REGENERATION OF A PYRIDINE COFACTOR BY ELECTROCHEMICAL REDUCTION

[75] Inventors: Alain Bergel; Maurice Comtat, both of Toulouse; Jean-Louis Seris, Jurancon, all of France

[73] Assignee: Societe Nationale Elf Aquitaine, Courbevoie, France

[21] Appl. No.: 491,270

[22] Filed: Mar. 9, 1990

[30] Foreign Application Priority Data

Mar. 13, 1988 [FR] France ................................ 89 03228

[51] Int. Cl.$^5$ ................................................ C25B 3/00
[52] U.S. Cl. .................................... 204/73 R; 204/74
[58] Field of Search ........................... 204/73 R, 74, 72

[56] References Cited

U.S. PATENT DOCUMENTS 4,464,235  8/1984  Simon et al. ...................... 204/73 R
4,490,464 12/1984  Gorton et al. .................. 204/153.12

Primary Examiner—John F. Niebling
Assistant Examiner—Steven P. Marquis
Attorney, Agent, or Firm—Oblon, Spivak, McClelland, Maier & Neustadt

[57] ABSTRACT

The invention relates to a process for the electrochemical regeneration of pyridine cofactors.

The process of the invention is characterized by carrying out a doubly mediated catalysis by means of a flavin and an oxidoreductase enzyme.

9 Claims, No Drawings

PROCESS FOR THE REGENERATION OF A PYRIDINE COFACTOR BY ELECTROCHEMICAL REDUCTION

The present invention relates to a process for the regeneration and reduction of nicotinamide adenine dinucleotide, a pyridine cofactor, by an electrochemical method.

The use of oxidation/reduction enzymes in organic synthesis is developing rapidly. These enzymatic synthesis processes employ pyridine cofactors such as NADH (nicotinamide adenine dinucleotide) or NADPH (nicotinamide adenine dinucleotide phosphate) involved in the oxidation/reduction mechanism. However, extrapolation of the results obtained in the laboratory to a larger scale necessitates, on the one hand regeneration of the pyridine cofactors, which are much too expensive to be used in stoichiometric amounts, and on the other hand reliable means of monitoring the reactions.

For this reason, the development of many studies for investigation of the optimal conditions for regeneration of these cofactors is currently taking place. This regeneration may be carried out chemically, enzymatically or electrochemically. Analysis of the advantages and drawbacks of these various methods shows that no general technique of regeneration is completely satisfactory, and it is advisable to envisage optimization of the overall direct reaction/regeneration system in each particular case.

For the reduction of NAD+, enzymatic methods have given the best results to date. Among the systems used, the following substrate/enzyme systems may be mentioned: formate/formate dehydrogenase, glucose-6-phosphate/glucose-6-phosphate dehydrogenase, glucose/glucose dehydrogenase, ethanol/alcohol dehydrogenase and hydrogen/hydrogenase.

Electrochemical processes appear attractive, at least theoretically, because they enable the regeneration rate to be fixed very readily by the choice of electrode potential. Moreover, they offer the possibility of ready monitoring of the reaction by measurement of the intensity of electrolysis with time. However, the advantages are limited by the incompatibility of some reactants capable of reacting directly with the electrode brought to the reduction potential; contamination of the electrode by adsorbable products and reactants and the lack of selectivity are other major drawbacks The latter problem is especially sensitive for reduction on account of the formation of the free radical intermediate NAD+, liable to dimerize rapidly, by one-electron transfer. The radical appears on the electrodes irrespective of their nature.

The control of electron transfer between the electrodes and NAD+ is important for carrying out the process of regeneration of NADH by reduction of NAD+.

To overcome these drawbacks and improve the transfer, the use of mediators such as methyl viologen, rhodium complexes or aminopteridine has been proposed. It should be noted, however, that the transfer with mediator improves performance only very modestly, and leads to passivation of the electrodes and to the appearance of by-products. By way of example, the work of S. KWEE and H. LUND (Bioélectrochem. Bioeng. 1974, 1, 87-95) may be mentioned. Other authors have proposed the use of a methyl viologen/enzyme system for the reduction reaction: H. SIMON, H. GUNTER, J. BADER and W. TISCHER (Angew. Chem. 1981, 20, 961-63), who describe catalysis of the reaction: $NAD^+ + H^+ + 2MV^{\cdot +} \rightarrow NADH + 2MV^{2+}$ by an enoate reductase (Clostridia) and regeneration of $MV^{2+}$ on a cathode:

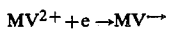

The problems caused by side reactions due to $MV^{\cdot +}$ limit the use of this type of process.

The Applicant has, for his part, in a pending French Patent Application No. 88/11,933 of 13.09.1988, proposed process for the regeneration of NADH by electrochemical reduction of NAD+ using a cytoplasmic hydrogenase enzyme acting as a mediator by providing for an electron relay between the electrode and the NAD+ cation which thereby avoids formation of the dimer (NAD):$_2$.

The object of the present invention is to overcome the above drawbacks and propose a doubly mediated catalytic system permitting regeneration of the cofactor by reduction of NAD+, avoiding the formation of by-products, but which, moreover, may be used in a process of oxidation of NADH.

The subject of the invention is a process for the regeneration of nicotinamide adenine dinucleotide (NAD+), or its derivatives such as nicotinamide adenine dinucleotide phosphate (NADP+), by reduction by carrying out the reaction: $NAD(P)^+ + H^+ + 2e \rightarrow NAD(P)H$, characterized by the use of the combination of a flavin and an oxidoreductase enzyme (ORE) in the reaction medium.

Catalysis of the reactions is accomplished by electron transfer between the metal of the electrode, the flavin and the NAD+/NADH system. The mechanism involved may be represented in outline in the following scheme, in which the flavin is symbolized by Fla:

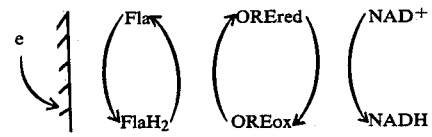

When the reduction of NAD+ is carried out with FlaH$_2$, it is necessary to have a solution containing a high concentration of FlaH$_2$ in the medium. The following process is then carried out:

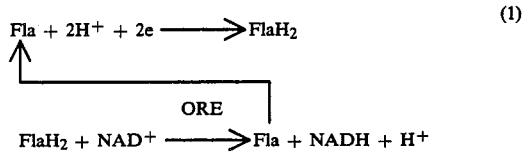

The essential advantage lies in the absence of the dimer (NAD)$_2$, which usually appears during direct reduction on an unmodified electrode. The reduction overvoltage is decreased by 0.1 volt relative to the direct reduction process.

The process of the invention is carried out in the presence of a flavin, that is to say a compound of the riboflavin family as described in Kirk-Othmer 3rd edition vol. 24 pp 108-121, capable of changing readily by electron transfer or enzymatic catalysis from an oxidized form Fla to a reduced form FlaH₂ and vice versa. Compounds such as flavin mononucleotide (FMN) or flavin adenine dinucleotide (FAD) are preferably used.

These biological molecules, which are generally employed in organisms in which the enzymes used participate, are naturally more biocompatible than organic compounds such as methyl viologen, and hence have the advantage of minimizing risks of side reactions.

The process of the invention utilizes in the medium, together with the flavin, an enzyme, designated by convention ORE, capable of catalysing the oxidation/reduction reaction enabling NAD⁺ and FlaH₂ to be converted to NADH and Fla, that is to say NAD⁺ to be reduced and FlaH₂ to be oxidized simultaneously.

Among OREs which are usable in the process of the invention, there may be mentioned Photobacterium pischiri FMN oxidoreductase, ferredoxin:NADP⁺reductase (FNR) extracted from spinach leaves and Pseudomonas oxalaticus formate dehydrogenase (FDH). The latter enzyme catalyses the oxidation of the formate ion according to the following reaction:

$$HCO_2^- + NAD^+ \xrightarrow{FDH} CO_2 + NADH.$$

According to the literature, this enzyme is very specific for the formate ion, and only the formate ion and NADH are capable of playing the part of electron donor, whereas it accommodates a much larger number of electron acceptors (flavins, dyes, oxygen).

It was thus surprising to find that this enzyme was capable of catalysing a reduction reaction in which the formate ion does not participate.

The enzyme formate dehydrogenase extracted from Pseudomonas oxalaticus will preferably be used. This enzyme has a molecular weight Mw of 315,000 daltons and contains two flavin mononucleotides, from 18 to 25 iron atoms and from 15 to 20 sulphur atoms, organized in twice two subunits of Mw 100,000 and 59,000 daltons It is essential that the two components, flavin and ORE, are introduced simultaneously; in effect, the electrochemical process does not enable an adequate reduction of NAD⁺ to be obtained in the absence either of the flavin or of the ORE enzyme.

One of the important features of the process of the invention is that the reduction reaction of NAD⁺ is carried out by means of a catalytic system generally used for the oxidation of NADH, by reversal of the equilibrium as a result of the use of thin-layer electrochemistry. The oxidation/reduction reaction (1) described on page 3 is a reversible reaction whose thermodynamic equilibrium favours the oxidation reaction of NADH to NAD³⁰. When it is desired to employ it in the reduction direction, it is important to have a high concentration of FlaH₂ in the medium.

Thin-layer electrochemistry is characterized by the use of a cell such that the surface area (S) of the electrode is large in comparison to the reaction volume (V). The S/V ratio of such a cell is estimated to be between 1,000 and 10,000 m⁻¹.

This device enables a virtually zero concentration of Fla to be retained in the reaction volume as a whole, and incidentally provides for a very high and homogeneous concentration of FlaH₂ which causes a shift in the equilibrium:

$$FlaH_2 + NAD^+ > Fla + NADH + H^+$$

The process of the invention will be carried out at a substantially neutral pH. It will generally be between 5 and 9, corresponding to the stability of enzymes used in the process and to their optimal pH for functioning.

The respective amounts of NAD⁺ and FAD in the reaction medium will be selected in such a way as to optimize the overall reaction rate, this being done in accordance with the kinetics of the two successive reactions in the presence of the ORE enzyme in question.

When, in the context of a process for the enzymatic reduction of a substrate, the regeneration of NADH is to be carried out by reduction of NAD⁺ using the process of the invention, the amounts of flavin and NAD⁺ used in the reaction medium are small compared with the amounts of substrate to be converted. In effect, the flavin and NAD⁺ are constantly converted and regenerated and simply play the part of a catalyst in the conversion, the reducing agent being the cathode which supplies the necessary electrons The substrate/flavin or substrate/NAD⁺ weight ratio will generally be between 100 and 10,000.

In addition, the ORE enzyme will generally be used in a catalytic amount; the medium will in general contain from 10 to 500 U/ml thereof.

The features of the process of the invention will be more fully understood on reading the examples which follow, given simply by way of illustration.

Examples 1 to 11

This series of examples illustrates the doubly mediated electrochemical reduction of NAD⁺ by means of FADH₂ and the enzyme formate dehydrogenase.

The general working conditions in these examples are as follows:

platinum electrode employed in a thin layer: V/S ratio of the order of 3,500 m⁻¹:

NAD⁺ concentration 5 mM medium: 0.2 M phosphate buffer, pH 7.0

The medium also contains:

the enzyme formate dehydrogenase FDH, and a flavin, FAD, in variable amounts according to the examples, as specified in Table 1 below.

In practice, in the first place, FADH₂ is formed by the electrochemical reduction of FAD, FADH₂ then reducing NAD⁺ to NADH through the action of the enzyme FDH.

The conversion by reduction is assessed by the initial rate of formation of NADH(v), which is measured by monitoring the changes in absorbance at 340 nm during an electrolysis performed at −0.6 V/SCE (saturated calomel electrode).

The results obtained by varying, on the one hand the concentration of flavin FAD, and on the other hand the concentration of FDH, are collated in Table 1 below.

TABLE 1

| Doubly mediated reduction of NAD⁺ with FADH₂ + FDH | | | | | | | | | | | |
|---|---|---|---|---|---|---|---|---|---|---|---|
| FAD (mM) | 0 | 0 | 3.0 | 7.0 | 1.75 | 2.25 | 3.0 | 4.5 | 5.25 | 6.0 | 8.0 |
| FDH (mg/ml) | 40 | 60 | 0 | 0 | 40 | 40 | 40 | 40 | 40 | 40 | 40 |
| v | 0 | 0 | 0 | 0 | 5.3 | 6.6 | 7.1 | 10.0 | 12.4 | 13.8 | 15.4 |

TABLE 1-continued

Doubly mediated reduction of $NAD^+$ with $FADH_2 + FDH$ (μM. min$^{-1}$)

Comparative Examples 1 to 4 show that, in the absence of either the flavin or the enzyme, no NADH is formed. The simultaneous presence of both molecules is essential for the process to be carried out.

Examples 5 to 11 illustrate the influence of the FAD concentration on NADH formation.

Example 12

This example illustrates the regeneration of a pyridine cofactor by thin-layer electrochemical reduction employing flavin mononucleotide (FMN) as flavin and the enzyme Photobacterium pischeri NADH:FMN oxidoreductase.

The working conditions were as follows:
$NAD^+$: 5 mM, FMN: 2 mM, enzyme: 1.3 U/ml,
0 1 M Phosphate buffer medium, pH 7.2
Electrolysis at $-0.65$ V/SCE
Initial rate of reduction of $NAD^+$: $2.6 \times 10^{-3}$ μmol. min$^{-1}$. U$^{-1}$

Example 13

This example illustrates the regeneration of NADPH (nicotinamide adenine dinucleotide phosphate) by the thin-layer electrochemical reduction of $NADP^+$ employing FMN as flavin and the enzyme referred to in Example 12 above.

The working conditions were as follows:
$NADP^+$: 5 mM, FMN: 2.5 mM, enzyme: 2.6 U/ml,
Medium: 0.1 M phosphate buffer, pH 7.2
Electrolysis at $-0.65$ V/SCE
The initial rate of reduction of $NADP^+$:
$1.2 \times 10$ μmol.min$^{-1}$.U$^{-1}$

Example 14

This example illustrates the regeneration of NADPH by thin-layer electrochemical reduction of $NADP^+$ employing FMN as flavin and the enzyme ferredoxin:-$NADP^+$reductase extracted from spinach leaves The working conditions are as follows:
$NADP^+$ 5 mM, FMN: 2.5 mM, enzyme: 4 U/ml,
Medium: 0.1 M phosphate buffer, pH 7.2
Electrolysis at $-0.65$ V/SCE
The initial rate of reduction of $NADP^+$:
$5.5 \times 10^{-3}$ μmol.min$^{-1}$.U$^{-1}$

We claim:

1. Process for the regeneration of the pyridine cofactor nicotinamide adenine dinucleotide or its derivatives by electrochemical reduction, comprising conducting said electrochemical reduction in a medium comprising a flavin and an oxidoreductase enzyme.

2. Process according to claim 1, wherein the flavin is flavin adenine dinucleotide (FAD).

3. Process according to claim 1, wherein the flavin is flavin mononucleotide (FMN).

4. Process according to one of claims 1 to 3, wherein the oxidoreductase enzyme is a formate dehydrogenase (FDH) extracted from Pseudomonas Oxalaticus.

5. Process according to one of claims 1 to 3, wherein the oxidoreductase enzyme is an NAD:FMN oxidoreductase extracted from Photobacterium pischeri.

6. Process according to one of claims 1 to 3, wherein the oxidoreductase enzyme is ferredoxin:$NADP^+$reductase (FNR).

7. Process according to one of claims 1 to 3, wherein the electrochemical reaction is carried out in a thin-layer electrochemical device.

8. Process according to claim 7, wherein that the device is provided with a cell and a platinum electrode such that the S/V ratio is between 1,000 and 10,000 m$^{-1}$.

9. Process according to one of claims 1 to 3, wherein the content of oxidoreductase enzyme in the medium is between 10 and 500 U/ml

* * * * *